United States Patent [19]

Edelman

[11] 4,073,292
[45] Feb. 14, 1978

[54] CONTROL APPARATUS FOR THE AUTOMATIC TREATMENT OF DIABETES

[76] Inventor: William Edelman, 43 Livingston Lane, Englishtown, N.J. 07726

[21] Appl. No.: 736,996

[22] Filed: Oct. 29, 1976

[51] Int. Cl.² .............................................. A61M 5/00
[52] U.S. Cl. .............................. 128/214 E; 128/2 F; 128/2 R; 128/DIG. 13
[58] Field of Search ................... 128/2 R, 2 L, 214 E, 128/214 B, DIG. 13; 356/39, 41, 42

[56] References Cited

U.S. PATENT DOCUMENTS

| 3,920,969 | 11/1975 | Berglas | 128/2 R |
| 3,958,560 | 5/1976 | March | 128/2 L |
| 4,001,801 | 1/1977 | Moulet | 128/DIG. 13 |
| 4,003,379 | 1/1977 | Ellinwood | 128/2 R |

*Primary Examiner*—Benjamin R. Padgett
*Assistant Examiner*—Josephine Lloyd Barr
*Attorney, Agent, or Firm*—Charles I. Brodsky

[57] ABSTRACT

The control apparatus of the invention comprises a feedback system to maintain the level of glucose in a diabetic within predetermined limits. Surgically implanted in the body are a means for sensing glucose levels and a means for dispensing insulin in an amount determined by the sensing mechanism. The sensing mechanism employs a chemical solution, which, like the insulin, is stored within a reservoir forming part of the surgical implant. Means are additionally provided to couple these reservoirs to the surface of the skin so as to permit their rechargings at regular time intervals. Integrated circuit technology is employed to translate an indication of an unacceptable glucose level into an automatic injection of insulin, with the electronics being of the type capable of being powered by batteries of the kind employed in pacemaker technology.

8 Claims, 5 Drawing Figures

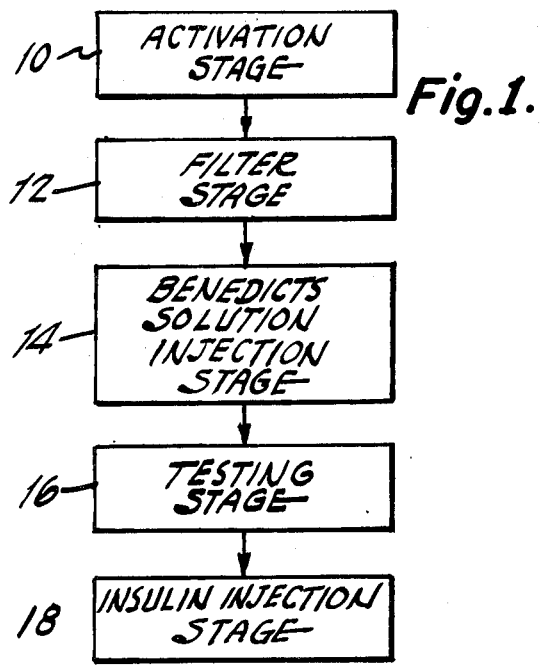
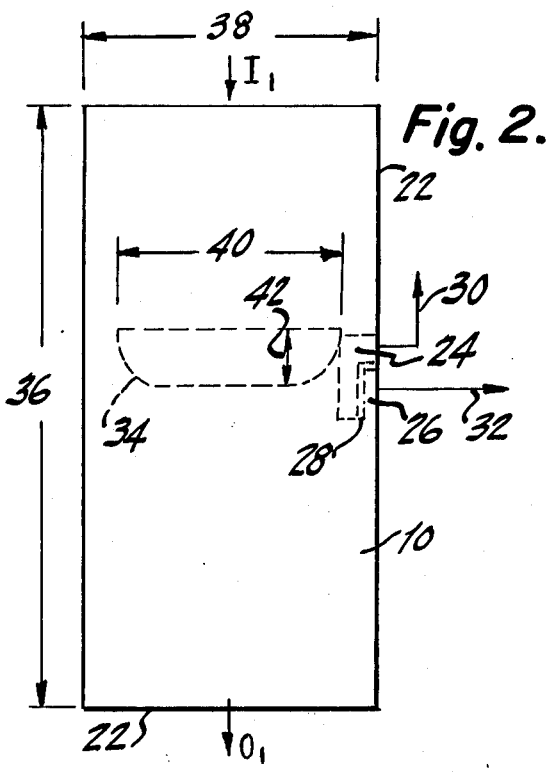
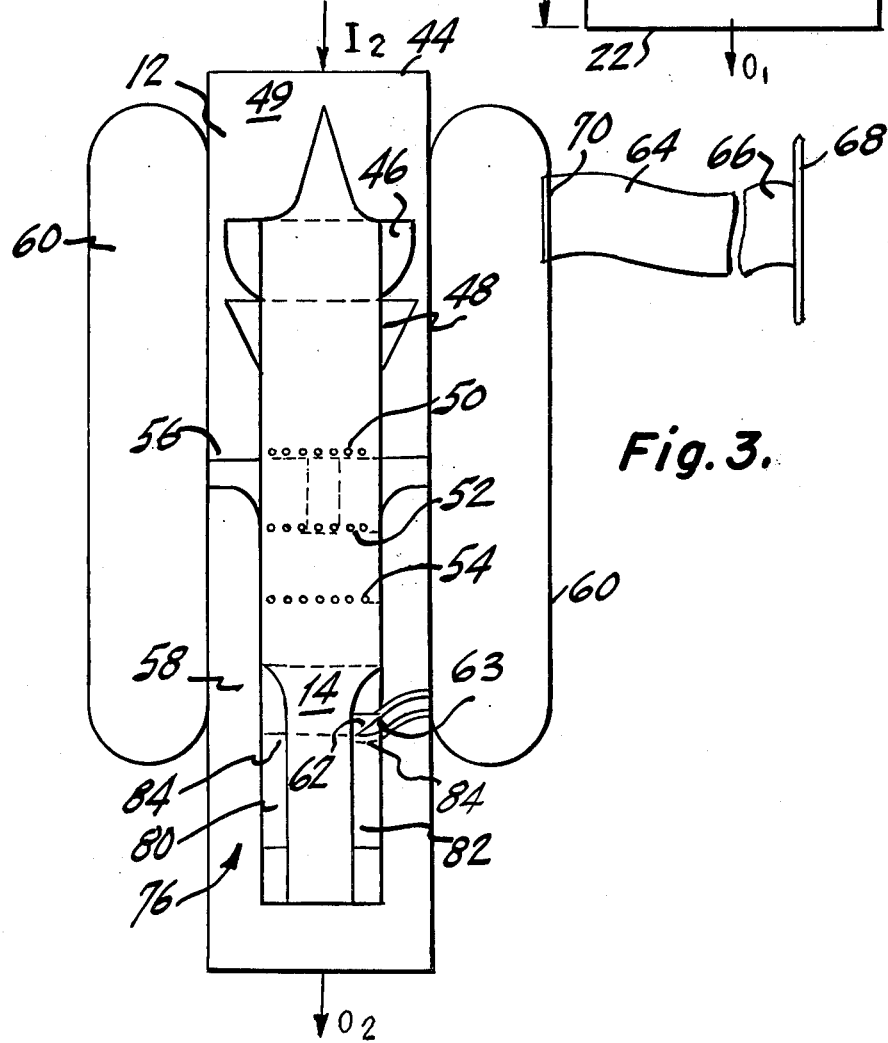

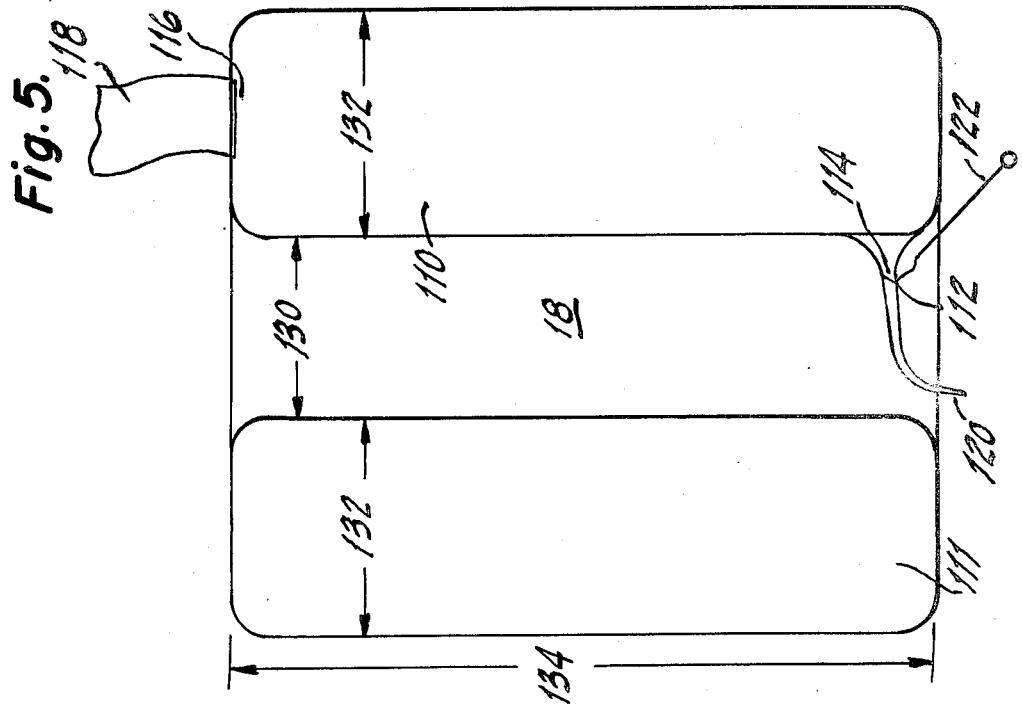
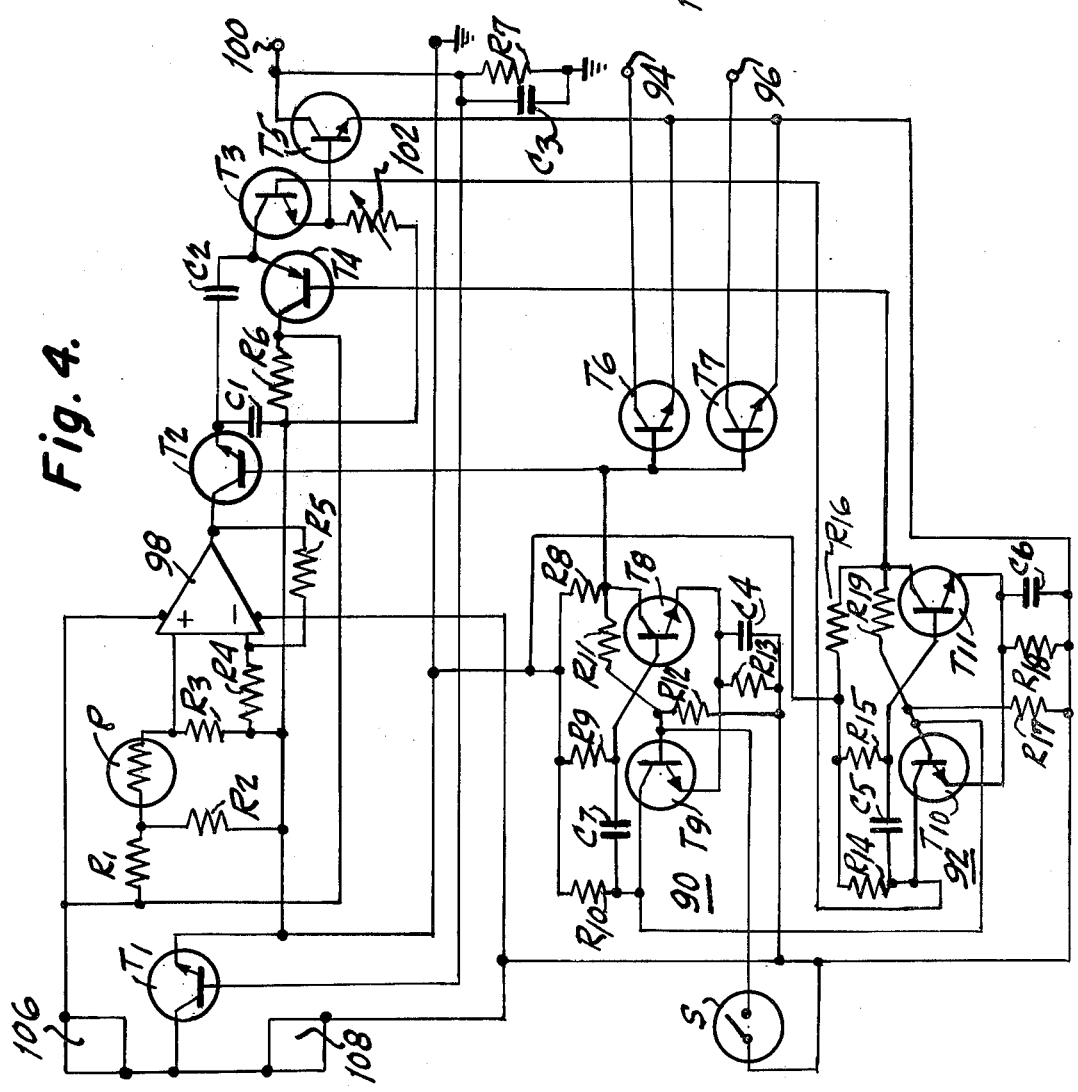

CONTROL APPARATUS FOR THE AUTOMATIC TREATMENT OF DIABETES

FIELD OF THE INVENTION

This invention relates to the automatic maintenance of glucose level in a diabetic within predetermined limits and, more particularly, to control apparatus for monitoring the body's sugar level during a given period, and if need be, for injecting suitable doses of insulin to suppress any excess amount of glucose — all without any involvement by the diabetic.

BACKGROUND OF THE INVENTION

As is well known and understood, throughout the history of diabetic control, the classic approach has been to provide insulin injections on a regular timed basis. In particular, the control is such that the level of glucose in the blood fluctuates from a low level, just after an insulin injection, to a very high level, just before a second injection is made. Strict time schedules are observed for the necessary injections, but even when the schedules are strictly adhered to, the complaints are legion as to the need to follow this type of control regimen.

SUMMARY OF THE INVENTION

As will become clear hereinafter, the control apparatus of the present invention automatically provides the necessary insulin injection without the need for any involvement by the diabetic. As will be seen, control apparatus operates internally of the body to automatically react urine from the kidneys with Benedict's Solution, and to employ a light emitter — photocell arrangement to indicate the glucose level in accordance with the amount of light passing the mixture. In response to the signal developed by the photocell, a valve is opened to inject a measured amount of insulin into a major artery, so as to maintain the level of glucose substantially constant. As will be described, such measurement and control is had whenever the person urinates, and because of the frequencies thereof and the relative time lapses therebetween, the apparatus of the invention is able to monitor the glucose level several times a day, thereby controlling it to within a small range. Both the Benedict's Solution and the insulin are stored in reservoirs which are surgically implanted within the diabetic, and with the pH level of the insulin raised so as to extend its stability over longer periods of time. Both reservoirs are situated within the body in a position so that they can be recharged for reuse.

In accordance with the operation of the invention, various stages contribute to the overall regulation of glucose level. In order of operation, the sequence employs: (1) an activation stage, wherein the apparatus is triggered into action; (2) a filter stage, wherein materials capable of undesirably influencing a determination of glucose level are filtered out; (3) the Benedict's Solution injecting stage, wherein the solution is added to the urine for the monitoring of glucose; (4) the testing stage, wherein the light passing the mixture and impinging the photocell is converted to an electronic control signal to regulate the amount of insulin to be injected; and (5) the insulin injection stage, wherein the amount of insulin injected into the bloodstream is regulated.

BRIEF DESCRIPTION OF THE DRAWINGS

These and other features of the present invention will be more clearly understood from a consideration of the following description taken in connection with the accompanying drawings in which:

FIG. 1 is a flowchart illustrating the sequence of events in the operation of the control apparatus;

FIG. 2 illustrates the activation stage;

FIG. 3 shows a combined filter stage, a Benedict's Solution injecting stage and a test system stage according to the invention;

FIG. 4 illustrates one arrangement for the testing stage electronic control system; and FIG. 5 shows the insulin injection stage.

DETAILED DESCRIPTION OF THE DRAWINGS

Before considering a detailed description of the various stages which comprise the control apparatus of the invention, it will first be understood that the apparatus to be described operates with active mechanical controls, the process beginning with the initial operation via the activation stage 10 of FIG. 1. Here the control apparatus includes a small microswitch which is momentarily activated by the passage of urine — for example, through the ureter tube located after the bladder. The filter stage 12, however, is located in the ureter tube before the bladder and serves to separate out all material present in the urine which is larger than the glucose complexes. The tripping of the switch brings into operation the Benedict's Solution injection stage 14, where the filtrate is mixed with Benedict's Solution, the effect being to darken the glucose complexes present. The treated solution then passes to the testing stage 16, wherein a photocell is opposed to a light emitting source, in accordance with which the signal generated indicates the extent of glucose present and the amount of insulin to be injected as a control, as a function of the light which passes. That is, as the glucose level rises and falls, the transparency of the mixture decreases and increases, respectively, thereby controlling the light passing through and impinging onto the photocell — with the constraints on the electronic circuitry included within the testing stage 16 being such that should the photocell detect a minimum amount of light, a control signal would be developed to direct the injection of a maximum dosage of insulin, and vice versa. Once the amount of glucose present has thus been determined, the control signal representative thereof is coupled to the insulin injection stage 18 so as to regulate the injection of insulin into a major artery. Here, a microvalve is operated by the signal control to permit insulin to flow into the artery for a predetermined time interval, with the entire operation being then terminated by the closing of this microvalve after the insulin has thus been injected. This terminates the operation, until the microswitch in the activation stage 10 is triggered again by the flow of urine, in making a further glucose measurement.

Referring now more particularly to the activation stage of FIG. 2, it will be understood that the function of the activation stage is to initiate the sequence of events which ultimately results in the injection of insulin into the bloodstream to supress high levels of glucose. Due to the nature of the urine fluid to be tested, and because of the fact that urination is what activates the entire mechanism, the activation station is placed in an area where it is directly exposed to periodic urinary flow — the urinary tract most suitable being directly after the bladder, in the ureter. The activation stage 10 is encompassed within an elastic material 22, chosen with a mind towards minimizing the possibility of rejection by the body — and a material such as Dacron might be used. By using an elastic material, the walls of the stage 10 can move within the areas of the body organs, whereas using a non-rejection type material permits it to be implanted in the area where the section of the ureter will be removed.

A pair of electrical contacts 24, 26 are incorporated at the sides of the implanted stage 10, being separated by a gap 28, encased in order to prevent against the urine acting as an electrolyte to form an electrical connection between the contacts 24, 26. A pair of cable connections 30, 32 couple to the contacts 24, 26 to complete an electrical circuit when the contacts are closed under the flow of urine. More particularly, included within the implanted activation stage 10 is an inverted cup body 34 arranged to catch the flow of urine entering the activation stage from the direction indicated by the arrow I, and exiting in the direction indicated by the arrow $O_1$. In response to the pressure force exerted on the cup by the urinary flow, the cup 34 will pivot so as to force the contact 24 across the gap 28 to connect to the contact 26, and thus close the circuit. In order to lessen any strain upon the contact 24, the cup 34 could be perforated to allow some urine to pass through in the direction of the arrow $O_1$, and thereby reduce much of the force that would otherwise be exerted upon the contact 24. Also, a large cross-sectional area of the cup 34 is arranged to force against the contact 24, so as to maintain integrity of operation over the years of expected use of the invention. Additionally, as a design feature, the cable connections 30, 32 are made to the contacts 24, 26 through hermetic openings so as to reduce any urinary fluid from penetrating outside the vessel walls 22. To reduce the possibility of the urine from corroding the insulation at the cable connections 30, 32, some form of resistant plastic (e.g. polyurethane) might be employed. In one embodiment of the invention, the distance 36 in FIG. 2 was fabricated to be approximately 1 inch in length, the distance 38 was fabricated to be approximately 0.5 inches, the dimension 40 was selected to be 0.375 inches and the dimension 42 was selected as 0.09375 inches.

Referring to the filter stage 12 of FIG. 3, it will be appreciated that the function of the filter stage is to isolate a usable portion of urine for testing by separating out urine components larger in size than the glucose complexes. From its output, the filtrate moves through the activation stage 10 into the Benedict's Solution stage 14 and the testing stage 16 where the actual glucose measurement takes place. In FIG. 3, therefore, it will be seen that the housing 44, — again constructed of an elastic composition (and of Dacron or similar material so as to prevent rejection by the body) — encompasses a series of cup collectors 46, 48 arranged in an aerodynamic cone configuration 29 to capture the urine as it flows in the direction indicated by the arrow $I_2$ towards the direction indicated by the arrow $O_2$. From the cup collectors 46, 48, the urine flows through a plurality of filters 50, 52, 54, each of increasing fineness, and suspended by a plurality of supports 56, 58 provided as an integral portion of the interior unit of the housing 44.

It is important to prolong the life of the filter stage 12 that it be located in an area where the urine flow is constant, rather than as where the flow is periodic or under pressure in nature — for example, as the urine flow would be if the filter stage were positioned in the ureter located directly after the bladder. Thus, the location of the filter stage 12, according to the invention, should be before the bladder, but after the kidney, along the vessel known as the ureter before the bladder penetration. (Then, it is only the filtered urine which operates the activation stage 10.) It will also be noted that stress problems are not as acute with the filter stage 12 as with the activation stage 10 because the filter stage 12 has no moving parts subject to failure.

Also shown in FIG. 3 is the Benedict's Solution injecting stage 14. As shown, there is included a reservoir 60 for storing the Benedict's Solution until required by the system after the activation stage 10 has engaged the entire apparatus. At the lower portion of the reservoir 60 is a one-way valve 62, which is normally closed to the flow of solution from the reservoir 60, but which, however, is opened for a short time interval (less than one second) by the operation of a small magnetic control 63 to permit the solution to mix with the filtrate for the subsequent testing to occur. Reference numeral 64 identifies an elastic tube which leads from reservoir 60 to the surface of the skin 68 through which the supply of Benedict's Solution is replaced at regular intervals. At the surface of the skin, in the area indicated by reference notation 66, will be seen the tube 64 as it reaches the skin surface 68. In accordance with the invention, the location on the surface of the skin 68 above the point where the tube 64 extends is marked with a dye visible under ultraviolet light to indicate the location for recharging reservoir 60 through injection of fresh solution. A second one-way valve 70 is also included, through which a hypodermic administering agent, for example, may penetrate in injecting fresh solution into the reservoir 60 in charging the device, and which prevents any fluid from flowing back into the tube 64.

In one design of the invention, the end of the tube 64 extending towards the surface of the skin 68 is widened at its end so as to fit flush against the skin interior to enable suturing to the interior of the skin wall. The reservoir 60 is constructed of elastic material so as to permit an outward movement during its filling and an inward contraction during the time the solution is added to the filtrate in serving to force the solution through the oneway valve 62. For ease of construction, the Benedict's Solution injecting stage 14 could be located at the same location as the filter stage 12 — as shown, at the ureter before the bladder penetration. As with the activation stage 10 and the filter stage 12, the material of which the Benedict's Solution reservoir 60 is fabricated is selected of a material which will be accepted by the body, and not rejected by it.

The testing stage 16 of the control apparatus incorporates a test system (76 in FIG. 3) and the electronic circuitry (FIG. 4) which directs the entire operation, from activating the apparatus to injecting the insulin. Referring to FIG. 3, the test system 76 incorporates two reservoirs 80, 82 subsequent to the Benedict's Solution injecting stage 14, into which the treated filtrate is forced to flow through constructed regions 84 so as to facilitate the identification of any glucose present. Each of these reservoirs 80, 82 have associated with it a combination light-emitting diode and photocell arrangement, in accordance with the operation of which, the light from the diode diffuses through the treated filtrate to be incident upon the photocell. As will be readily understood, the intensity of the light impinging the photocell is dependent upon the color of the mixture — which in turn is related to the concentration of the glucose level. In particular, as Benedict's Solution changes color in the presence of a glucose complex, the degree of color change depends upon the relative concentration of that glucose complex in the urine being analyzed. In particular, the signal level developed by the photocell as the emitted light passes the admixture would be a maximum in the absence of glucose and would progressively decrease as the amount of glucose present becomes greater.

The electronic circuitry of FIG. 4, in part, translates the molar concentration of glucose present into the amount of insulin needed to be injected into the blood. In its operation, the electronic circuitry serves to direct the insertion of a predetermined amount of insulin for a given signal level from the photocell, and directs that the amount of insulin injected be accordingly reduced as the signal level from the photocell increases.

As will be understood, upon the activation of the system, when the switch contacts 24, 26 of FIG. 2 are closed, there is a resulting closure of the switch S (FIG. 4) to energize the multivibrators 90, 92. This provides an output control signal for the Benedict's Solution injecting stage magnet 63 at terminal 94 of some one second duration and a like output control signal at terminal 96 to energize the light emitting diode. During the time the light emitting diode is energized, the signal from the photocell P couples through an operational amplifier 98 in providing the output control signal at terminal 100 for controlling a valve opening at the insulin injecting stage for a time determined by the resistance setting of potentiometer 102, which is individually set to satisfy the diabetic needs of the individual being served. It additionally goes without saying that the duration of the output signal at terminal 100 will be proportional to the density of glucose in the urine such that the combination of the glucose complex present and the resistance setting of potentiometer 102 will regulate the amount of insulin injected as befits the individual's needs at any instant of time.

In one construction of the control apparatus, the signal developed at terminal 94 is employed to not only activate the light emitting diode, but to de-activate the activation stage 10 of FIG. 2 (by opening the closed circuit formed between cable connections 30, 32) so as to make the activation stage operate as a momentary switch. When the insulin injection is completed, the apparatus becomes recycled to its initial, quiescent condition, until the activation stage is once again set in motion by urinary flow to re-establish the operational sequence. In the system of FIG. 4, it will be appreciated that the electronic circuitry is powered by batteries 106, 108 of a kind commonly used in pacemaker technology. While applicant does not wish to be limited in his choice of component values, the following have proved useful in one embodiment of the invention, in which ten 1.4 volt batteries were employed in energizing the electronics.

Resistor R1 . . . 5.1 ohms
Resistor R2 . . . 5.6 ohms
Resistor R3 . . . 10 ohms
Resistor R4 . . . 1 kilohm
Resistor R5 . . . 68 kilohms
Resistor R6 . . . 100 ohms
Resistor R7 . . . 100 kilohms
Resistor R8 . . . 10 kilohms
Resistor R9 . . . 150 kilohms
Resistor R10 . . . 10 kilohms
Resistor R11 . . . 100 kilohms
Resistor R12 . . . 1 kilohm
Resistor R13 . . . 1 kilohm
Resistor R14 . . . 10 kilohms
Resistor R15 . . . 150 kilohms
Resistor R16 . . . 10 kilohms
Resistor R17 . . . 1 kilohm
Resistor R18 . . . 1 kilohm
Resistor R19 . . . 100 kilohms
Capacitor C3 . . . 20 microfarads
Capacitor C4 . . . 1 microfarad
Capacitor C5 . . . 1.6 microfarads
Capacitor C6 . . . 1 microfarad
Capacitor C7 . . . 1.6 microfarads
Transistors T1-T11. 2N1605
Operational Amplifier 98 . . . RCA Type CA3004

In addition, the light emitting diode employed was selected such that the emitted light would be sensitive to the particular range of colors that might be assumed by the Benedict's Solution mixture. The photocell P selected had an imput of 0.08-9 milliamperes, such that a current signal of 9 milliamperes is generated when the testing stage indicates a clear urine specimen, i.e., without glucose present. On the other hand, where the Benedict's Solution mixture was saturated with glucose, so that minimum light was registered by the photocell, then the photocell would provide an output current of 0.08 milliamperes.

As was previously mentioned, potentiometer 102 is pre-set in order to match the individual with his possible dosage needs of insulin during the day. This resistance is, in actuality, set with regard to the values employed for capacitors C1 and C2 — in particular, the maximum time during which the insulin injecting stage will be active is given by the expression 1.2 RC, wherein R represents the resistance value for the potentiometer 102 and C represents the capacitance values for capacitors C1 and C2. If it is assumed, for example, that 1cc of insulin is to be injected over a two second interval, then 1.2 RC would equal 2 seconds, and RC would equal 1.7. If the capacitance values for capacitors C1 and C2 were each selected to be 1 microfarad each, then the resistance value for potentiometer 102 for this person would be 1.7 ohms, a value readily available in variable resistance design.

As with the stages previously described, certain design considerations must be observed in order to maintain the integrity of the testing stage operation. One area of concern is to prevent any fluid from infiltrating the structure of the light emitting diode — photocell arrangement and causing a possible failure of the testing system. Thus, in an actual design for surgical implantation, the photocell and light emitting diode should be hermetically sealed, and with a sealant able to withstand exposure to any urinary flow. The testing stage, because of the design employed, will be understood as being a part of the actual filter stage and Benedict's Solution injecting stage construction, as implicit in its illustration as part of FIG. 3. In other words, the testing stage is located within the filter stage housing in the ureter, prior to the bladder.

The insulin injecting stage 18 of FIG. 5 is similar in construction to the Benedict's Solution injecting stage 14 of FIG. 3, in its usage of an elastic reservoir 110 to store a fluid, which is permitted to exit via means of a one-way valve 112 controlled by energization of a small magnet 114. Similarly, the reservoir 110 is provided with a second one-way valve 116 which permits fluid — in this case insulin — to be injected into the reservoir 110 while at the same time, not permitting any to flow in an opposite direction. A tube 118 extends from the reservoir 110 to the surface of the skin where an arrangement analogous to that with the Benedict's Solution injection could be utilized — that is, the employment of an identifying mark visible under ultraviolet light through which an attending physician could provide an insulin injection to recharge the reservoir. A second tube 120, directs the insulin to be injected into the flow of blood in an artery, preferably, the aorta from whence it can quickly flow to all areas of the body. The cable connection 122 couples the electrical control signal from output terminal 100 of FIG. 4 to activate the magnetic control 114 in regulating the injection of insulin in accordance with the duration of the control signal applied. A pair of reservoirs 110, 111 are shown in FIG. 5, both of which will be understood to be similarly constructed. The dimensions 130, 132 and 134 were selected to be 0.5 inches, 0.75 inches and 2.25 inches, respectively.

As far as the insulin storage in reservoir 110 is concerned, recent advances have been noted in insulin preparation research to the point that it is possible to store insulin at body temperatures for up to twelve months without it losing more than 60% of its starting strength by raising the pH level of the insulin employed. If it is assumed that the Benedict's Solution injection stage will be activated on the average of 5 times per day, and that a capacity of 30cc of Benedict's Solution could be stored, then by establishing the physical dimensions and component selection of the electronic components employed, it would be possible to design the Benedict's Solution construction to retain sufficient solution for a 30 test supply before a need for recharging. It should be clearly apparent that once the implantation is completed, the diabetic condition is monitored and regulated automatically, without any need for daily injections or changes in prescribed diet.

In connection with the implantation of the insulin injecting stage 18, it will first be recognized that the pressures exerted on the aorta due to the reservoir charging may result in some form of fatigue within the system of the body's metabolism. In order to inhibit this, a sheath fitting placed around the aorta would permit expansion of the reservoir 110 without any pressing against the aorta itself. Care must also be taken to insure that the insulin will continue to flow through the valve 120 even though there be a slight imperfection or break in the penetration into the aorta.

In considering the invention, it has been determined that the electronic circuitry of the control apparatus should be located in an area of comparative proximity to the stages located near the aorta and in the ureters. The most convenient place for the electronics will thus be seen to be in the abdominal cavity. The battery system to energize the electronics should, also, be located as nearly as possible to the electronic circuitry employed. For the components listed previously, two packs of five batteries in series were employed in providing the appropriate energization. Furthermore, the wiring employed to couple signals between stages and the electronics with as little hindrance as possible and yet able to withstand the constant material stresses while maintaining integrity for the life of the instrument are readily available in the field of pacemaker technology and can be utilized equally as well with the apparatus described herein.

While there has been described what is considered to be a preferred embodiment of the present invention, it will be readily understood that changes may be made by those skilled in the art without departing from the scope of the teachings herein. For at least such reason, therefore, this invention should be read in light of the claims appended hereto.

I claim:
1. Control apparatus for the automatic treatment of diabetes, comprising:
   first means for admixing a urine sample from a living body with a chemical solution, a characteristic of which with respect to light varies as a function of the molar concentration of glucose complexes present in said sample;
   second means providing said chemical solution;
   third means providing a source of light;
   fourth means exposed to said source of light via the admixture of said first means and responsive to the light impinging thereon for generating a control signal representative of the molar concentration of said glucose complexes present;
   fifth means providing a source of modified insulin of increased pH; and
   sixth means responsive to said control signal for automatically injecting a predetermined amount of said modified insulin into an artery of the body to maintain the level of glucose complexes within the blood within prescribed limits;
   with said first, second, third, fourth, fifth and sixth means, being adapted to be surgically implanted within the body and with said second and fifth means being replenishable with chemical solution and insulin, respectively, without the need for additional surgical procedures.
2. The apparatus of claim 1 wherein said second means provides a chemical solution whose transparency to light varies inversely with the molar concentration of glucose complexes with which it may be admixed, and wherein said fourth means responds to the amount of light impinging thereon.
3. The apparatus of claim 1 wherein said first means includes seventh means for filtering material from a urinary fluid larger in size than said glucose complexes in providing said urine sample for admixture.
4. The apparatus of claim 1 wherein said sixth means automatically injects a predetermined amount of said modified insulin into the aorta of the body.
5. The apparatus of claim 1 wherein each of said second and fifth means include seventh means for storing a given amount of chemical solution and insulin, respectively, and eighth means coupling said storage means to the skin surface of the body for recharging said storage means by fluid injections administered thereat.
6. The apparatus of claim 1 wherein said first means is activated to provide said admixture at the time of body urination.
7. The apparatus of claim 1 wherein said sixth means is adjusted to prescribe the predetermined amounts of modified insulin to be injected in response to said control signal prior to its being surgically implanted into the body and in accordance with the particular needs of the individual into whose body the implantation is to proceed.
8. The apparatus of claim 2 wherein said third means includes a lightemitting diode and said fourth means includes a photocell.

* * * * *